(12) United States Patent
Law et al.

(10) Patent No.: US 6,465,011 B2
(45) Date of Patent: *Oct. 15, 2002

(54) FORMULATIONS COMPRISING LIPID-REGULATING AGENTS

(75) Inventors: Devalina Law, Libertyville; Steven L. Krill, Gurnee; Eric A. Schmitt, Libertyville, all of IL (US); James J. Fort, Midlothian, VA (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/320,188

(22) Filed: May 29, 1999

(65) Prior Publication Data

US 2001/0006662 A1 Jul. 5, 2001

(51) Int. Cl.[7] .................. A61K 9/20; A61K 9/127; A61K 9/48; A61K 9/50; A61K 31/12

(52) U.S. Cl. .................. 424/465; 424/464; 424/451; 424/499; 424/489; 424/501; 424/502; 424/450; 514/681

(58) Field of Search ................ 424/451, 464, 424/489, 450, 499, 501, 502, 465; 514/681, 510

(56) References Cited

U.S. PATENT DOCUMENTS

| | | |
|---|---|---|
| 4,058,552 A | 11/1977 | Mieville |
| 4,800,079 A | 1/1989 | Boyer |
| 4,895,726 A | 1/1990 | Curtet et al. |
| 4,927,639 A | 5/1990 | Ghebre-Sellassie et al. |
| 4,961,890 A | 10/1990 | Boyer |
| 5,030,447 A | 7/1991 | Joshi et al. |
| 5,180,589 A | 1/1993 | Joshi et al. |
| 5,645,856 A | 7/1997 | Lacy et al. |
| 5,798,375 A | 8/1998 | Tsujita et al. |
| 5,807,834 A | 9/1998 | Morehouse |
| 6,074,670 A | 6/2000 | Stamm et al. |

FOREIGN PATENT DOCUMENTS

| | | |
|---|---|---|
| EP | 0 462 066 A1 | 12/1991 |
| EP | 0793958 | 2/1997 |
| WO | 8201649 | 5/1982 |
| WO | 96/36318 | 11/1996 |
| WO | 98/15264 | 4/1998 |
| WO | 98/31361 | 7/1998 |

OTHER PUBLICATIONS

K. R. Morris, et al., Characterization of humidity–dependent changes in crystal properties of a new HMG–CoA reductase inhibitor in support of its dosage form development, International Journal of Pharmaceuticals, vol. 108, No. 3, (1994) 195–206.

M. Sheu, et al., Characterization and dissolution of fenofibrate solid dispersion systems, International Journal of Pharmaceutics, 103 (1994) 137–146.

G. Palmieri, et al, Characterization and dissolution studies of PEG 4000/fenofibrate solid dispersions, S.T.P. Pharma Sciences 6 (3) 186–194 1996.

Primary Examiner—Thurman K. Page
Assistant Examiner—Amy Pulliam
(74) Attorney, Agent, or Firm—Wood, Phillips, Katz, Clark & Mortimer

(57) ABSTRACT

The present invention is directed to a solid formulation comprising the lipid-regulating agent dispersed in a hydrophilic, amorphous polymer in which said lipid-regulating agent is present as a meta-stable, amorphous phase.

9 Claims, 1 Drawing Sheet

FORMULATIONS COMPRISING LIPID-REGULATING AGENTS

FIELD OF THE INVENTION

The present invention relates to novel formulations comprising lipid-regulating agents.

BACKGROUND OF THE INVENTION

2-[4-(4-chlorobenzoyl)phenoxy]-2-methyl-propanoic acid, 1-methylethylester, also known as fenofibrate, is representative of a broad class of compounds having pharmaceutical utility as lipid regulating agents. More specifically, this compound is part of a lipid-regulating agent class of compounds commonly known as fibrates, and is disclosed in U.S. Pat. No. 4,058,552.

Fenofibrate has been prepared in several different formulations, c.f., U.S. Pat. Nos. 4,800,079 and 4,895,726. 4,895,726 discloses a co-micronized formulation of fenofibrate and a solid surfactant.

U.S. Pat. No. 4,961,890 discloses a process for preparing a controlled release formulation containing fenofibrate in an intermediate layer in the form of crystalline microparticles included within pores of an inert matrix. The formulation is prepared by a process involving the sequential steps of dampening said inert core with a solution based on said binder, then projecting said fenofibrate microparticles in a single layer onto said dampened core, and thereafter drying, before said solution based on said binder dissolves said fenofibrate microparticles, and repeating said three steps in sequence until said intermediate layer is formed.

European Patent Application No. EP0793958A2 discloses a process for producing a fenofibrate solid dosage form utilizing fenofibrate, a surface active agent and polyvinyl pyrrolidone in which the fenofibrate particles are mixed with a polyvinyl pyrrolidone solution. The thus obtained mixture is granulated with an aqueous solution of one or more surface active agents, and the granules thus produced are dried.

PCT Publication No. WO 82/01649 discloses a fenofibrate formulation having granules that are comprised of a neutral core that is a mixture of saccharose and starch. The neutral core is covered with a first layer of fenofibrate, admixed with an excipient and with a second microporous outer layer of an edible polymer.

U.S. Pat. No. 5,645,856 describes the use of a carrier for hydrophobic drugs, including fenofibrate, and pharmaceutical compositions based thereon. The carrier comprises a digestible oil and a pharmaceutically-acceptable surfactant component for dispersing the oil in vivo upon administration of the carrier, which comprises a hydrophilic surfactant, said surfactant component being such as not to substantially inhibit the in vivo lipolysis of the digestible oil.

Sheu, M. T., et al, *Int. J. Pharm.* 103 (1994) 137–146, reported that a dispersion of fenofibrate in PVP still maintains the same crystalline form of the drug itself.

Palmieri, G. F., et al, *Pharma Sciences* 6 (1996) 188–194, reported that a dispersion of crystalline fenofibrate could be prepared in PEG 4000. The authors concluded solid solutions in PEG are formed when the amount of fenofibrate is less than 15% and the dissolution rate is increased, particularly for the 90/10 carrier/drug ratio.

Gemfibrozil is another member of the fibrate class of lipid-regulating agents. U.S. Pat. No. 4,927,639 discloses a disintegratable formulation of gemfibrozil providing both immediate and sustained release, comprising a tablet compressed from a mixture of a first and second granulation, and a disintegration excipient operable to effect partial or complete disintegration in the stomach. The first granulation comprises finely divided particles of pure gemfibrozil granulated with at least one cellulose derivative, and the second granulation comprises finely divided particles of pure gemfibrozil granulated with a pharmaceutically-acceptable water soluble or insoluble polymer which are then uniformly coated with a pharmaceutically-acceptable (meth)acrylate copolymer prior to admixture with the first granulation. The first and second granulations are present in the final composition in a ratio of from about 10:1 to about 1:10.

U.S. Pat. 4,925,676 discloses a disintegratable gemfibrozil tablet providing both immediate and enteric release, which is compressed from a mixture of a first granulation of gemfibrozil with at least one acid-disintegratable binder, and a second granulation formed from the first granulation, but regranulated or coated with an alkali-disintegratable formulation of at least one substantially alkali-soluble and substantially acid-insoluble polymer.

Another class of lipid-regulating agents are commonly known as statins, of which pravastatin and atorvastatin are members. U.S. Pat. Nos. 5,030,447 and 5,180,589 describe stable pharmaceutical compositions, which when dispersed in water have a pH of at least 9, and include a medicament which is sensitive to a low pH environment, such as pravastatin, one or more fillers such as lactose and/or microcrystalline cellulose, one or more binders, such as microcrystalline cellulose (dry binder) or polyvinylpyrrolidone (wet binder), one or more disintegrating agents such as croscarmellose sodium, one or more lubricants such as magnesium stearate and one or more basifying agents such as magnesium oxide.

It is an object of the present invention to provide formulations of lipid-regulating agents having enhanced bioavailability when compared to commercially available formulations.

SUMMARY OF THE INVENTION

The present invention is directed to a solid formulation comprising the lipid-regulating agent dispersed in a hydrophilic, amorphous polymer in which said lipid-regulating agent is present as a metastable, amorphous phase. The size reduction obtained through the preparation of a dispersion is usually difficult to obtain. However, by using any technique that results in the dispersion of the lipid-regulating agent in an amorphous polymer, such as, for example, solvent evaporation or fusion, results in an increase in the dissolution rate and oral bioavailability of the said lipid-regulating agent.

The formulation may be administered directly, diluted into an appropriate vehicle for administration, encapsulated into hard gelatin shells or capsules, or compressed into tablets, for administration, or administered by other means obvious to those skilled in the art.

DETAILED DESCRIPTION OF THE INVENTION

Figure 1:
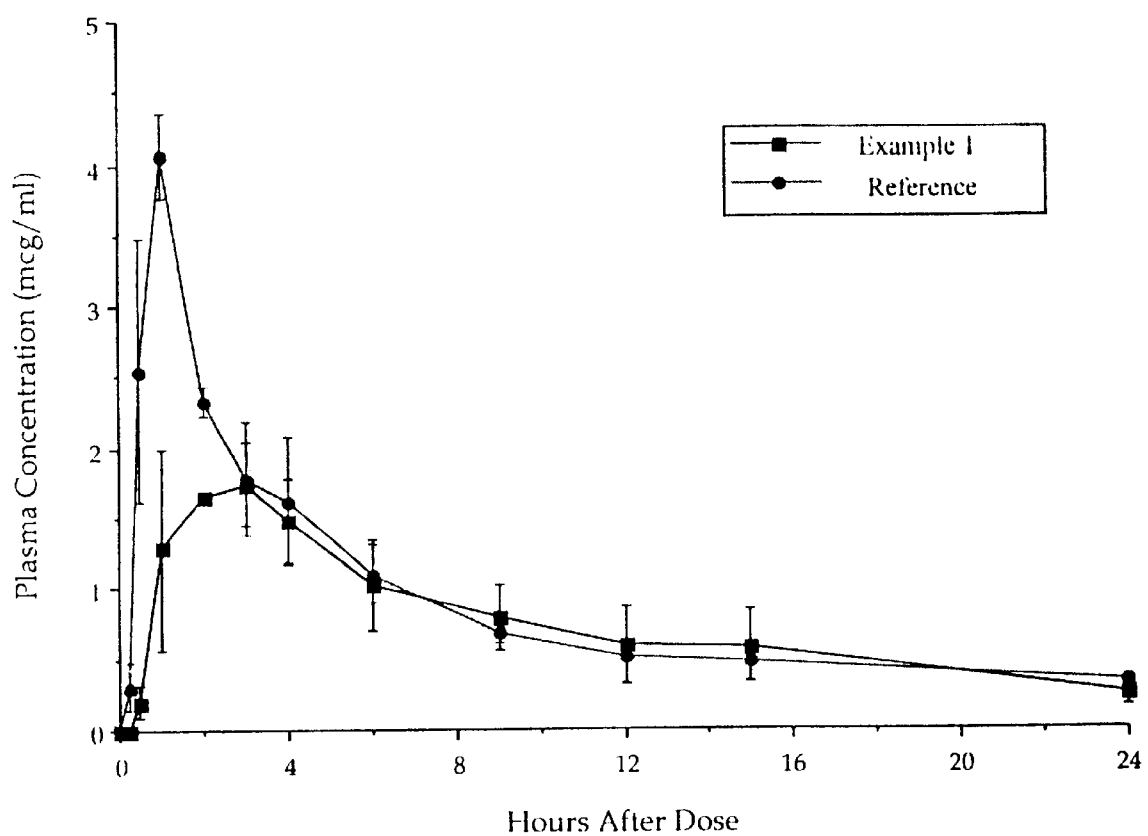
FIG. 1 is a graph showing the plasma concentration in fed dogs of the formulation of Example 1 and a reference compound.

The bulk lipid-regulating agent may be prepared by any available method, as for example the compound fenofibrate may be prepared by the procedure disclosed in U.S. Pat. No. 4,058,552, or the procedure disclosed in U.S. Pat. No. 4,739,101, both herein incorporated by reference.

The composition comprising the lipid-regulating agent is prepared by dissolving or dispersing the lipid-regulating agent and hydrophilic, amorphous polymer in a sufficient amount of solvent. The solvent is evaporated to yield a solid mass which is ground, sized and optionally formulated into an appropriate delivery system. Other techniques, known in the art, such as for example fusion or fusion-evaporation, may also be used.

The delivery system of the present invention results in increased solubility and bioavailability, and improved dissolution rate of the lipid-regulating agent.

If the solvent evaporation technique is used, suitable solvents include, for example, lower alkyl alcohols such as methanol, ethanol, or any other pharmaceutically-acceptable organic solvent in which the lipid-regulating agent and the polymers have appreciable solubility.

Suitable hydrophilic, amorphous polymers include, for example, polyvinylpyrrolidone (PVP), hydroxypropylmethylcellulose (HPMC), or other pharmaceutically-acceptable hydrophilic, amorphous polymers such as for example, Eudragits®.

Other pharmaceutically-acceptable excipients may be added to the formulation prior to forming the desired final product. Suitable excipients include, for example, lactose, starch, magnesium stearate, or other pharmaceutically-acceptable fillers, diluents, lubricants, disintegrants, etc., that might be needed to prepare a capsule or tablet.

The resulting composition comprising the lipid-regulating agent may be dosed directly for oral administration, diluted into an appropriate vehicle for oral administration, filled into capsules, or made into tablets for oral administration, or delivered by some other means obvious to those skilled in the art. The said composition can be used to improve the oral bioavailability and solubility of said lipid-regulating agent.

The invention will be understood more clearly from the following non-limiting representative examples:

EXAMPLE 1

A mixture (3 g) of fenofibrate and PVP (PF 17) in a ratio of 15:85 was dissolved in 4.5 mL of ethanol. The ethanol was evaporated under vacuum at 85° C. The resulting dry solid was then ground and sized through a 60–100 mesh screen. 446.7 mg of the granular formulation (containing 67 mg fenofibrate) was filled into individual capsules.

EXAMPLE 2

A mixture (3 g) of statin and PVP (PF 17) in a ratio of 15:85 is dissolved in sufficient ethanol. The ethanol is evaporated under vacuum at 85° C. The resulting dry solid is then ground and sized through a 60–100 mesh screen. The solid is then filled in capsules to obtain the desired unit dose.

EXAMPLE 3

Capsules prepared by the process described in Example 1, and from a commercial fenofibrate composition, Lipanthyl 67M (Groupe Fournier) (Reference), were administered to a group of dogs at a dose of 67 mg fenofibrate/dog. The plasma concentrations of fenofibric acid were determined by HPLC. Concentrations were normalized to a 6.7 mg/kg dose in each dog. FIG. 1 presents the resulting data in graph form. The results provided as mean±SD, n=6, were as follows:

Lipanthyl 67M (Reference):

Cmax=4.06±0.53 mcg/ml

Tmax=1.0±0.0 hr $t_{1/2}$=9.5 hr

AUC (0–24)=21.37±2.56 mcg·hr/ml

Capsule of Example 1:

Cmax=2.22±0.31 mcg/ml

Tmax=2.3±1.2

$t_{1/2}$=7.7 hr

AUC (0–24)=18.04 mcg·hr/ml

AUC relative to reference=84.40%.

What is claimed is:

1. A composition comprising a fibrate dissolved in a hydrophilic, amorphous polymer carrier in which said fibrate is present as a meta-stable, amorphous phase.

2. A composition of claim 1 wherein said fibrate is fenofibrate.

3. A composition of claim 1 wherein at least one or more of said hydrophilic polymers is selected from the group consisting of polyvinylpyrrolidone and hydroxypropylmethylcellulose.

4. A composition of claim 3 wherein at least one or more of said hydrophilic polymers is polyvinylpyrrolidone.

5. A delivery system comprising a composition of claim 1.

6. A delivery system of claim 5 wherein said delivery system is a capsule or tablet.

7. A method of treating hyperlipidemia comprising the administration of a composition of claim 1 to a patient.

8. A method of treating hyperlipidemia comprising the administration of a composition of claim 2 to a patient.

9. A method of treating hyperlipidemia comprising the administration of a composition of claim 6 to a patient.

* * * * *